(12) United States Patent
Sakai

(10) Patent No.: US 7,553,794 B2
(45) Date of Patent: Jun. 30, 2009

(54) HETEROPOLYACID AND OR ITS SALT SUPPORTED CATALYST, PRODUCTION PROCESS OF THE CATALYST AND PRODUCTION PROCESS OF COMPOUND USING THE CATALYST

(75) Inventor: Masaaki Sakai, Oita (JP)

(73) Assignee: Showa Denko K.K., Tokyo (JP)

( * ) Notice: Subject to any disclaimer, the term of this patent is extended or adjusted under 35 U.S.C. 154(b) by 659 days.

(21) Appl. No.: 10/539,706

(22) PCT Filed: Nov. 27, 2003

(86) PCT No.: PCT/JP03/15186

§ 371 (c)(1),
(2), (4) Date: Jun. 17, 2005

(87) PCT Pub. No.: WO2004/056474

PCT Pub. Date: Jul. 8, 2004

(65) Prior Publication Data

US 2006/0052240 A1    Mar. 9, 2006

Related U.S. Application Data

(60) Provisional application No. 60/436,633, filed on Dec. 30, 2002.

(30) Foreign Application Priority Data

Dec. 20, 2002   (JP) ............................. 2002-369424

(51) Int. Cl.

| | |
|---|---|
| B01J 23/00 | (2006.01) |
| B01J 21/18 | (2006.01) |
| B01J 21/02 | (2006.01) |
| B01J 27/00 | (2006.01) |
| B01J 27/198 | (2006.01) |
| B01J 27/19 | (2006.01) |
| B01J 21/00 | (2006.01) |
| B01J 23/02 | (2006.01) |
| B01J 23/06 | (2006.01) |
| C01B 15/16 | (2006.01) |
| C01B 25/26 | (2006.01) |
| C01B 15/14 | (2006.01) |
| C01B 33/20 | (2006.01) |
| C07C 69/74 | (2006.01) |
| C07C 61/00 | (2006.01) |
| C07C 61/08 | (2006.01) |
| C07C 51/245 | (2006.01) |

(52) U.S. Cl. ..................... 502/300; 502/180; 502/182; 502/204; 502/206; 502/208; 502/209; 502/210; 502/211; 502/232; 502/240; 502/247; 502/248; 502/254; 502/255; 502/340; 502/349; 502/350; 502/353; 423/305; 423/306; 423/307; 423/325; 423/326; 560/1; 562/400; 562/523

(58) Field of Classification Search ......... 502/208–214, 502/254, 255, 300, 305–323, 180, 182, 204, 502/206, 232, 240, 247, 249, 340, 349, 350, 502/353; 585/250, 275; 560/1; 562/400, 562/523; 423/305, 306, 307, 325, 326
See application file for complete search history.

(56) References Cited

U.S. PATENT DOCUMENTS 5,164,354 A * 11/1992 Aldridge et al. ............. 502/220

(Continued)

FOREIGN PATENT DOCUMENTS

CN      1203122 A      6/1997

(Continued)

OTHER PUBLICATIONS

Liu et al., "Structures and Catalytic Activity of Pt-Mo Bimetallic Ensembles Derived from a new Planar {PtMo6O24}8- Heteropolyanion Supported on Al2O3 and SiO2," Journal of Catalysis 135, 367-385 (1992).*

Primary Examiner—Steven Bos
Assistant Examiner—Anthony J Zimmer
(74) Attorney, Agent, or Firm—Sughrue Mion, PLLC

(57) ABSTRACT

A supported catalyst comprising a support having supported thereon at least one member selected from the group consisting of heteropolyacids and heteropolyacid salts, in which the heteropolyacid and/or heteropolyacid salt is substantially present in a surface layer region of the support to a depth of 30% from the support surface. The catalyst has a high performance when used for the production of compounds by various reactions.

16 Claims, 3 Drawing Sheets

U.S. PATENT DOCUMENTS

| | | | |
|---|---|---|---|
| 5,324,881 A * | 6/1994 | Kresge et al. | 585/721 |
| 5,366,945 A * | 11/1994 | Kresge et al. | 502/60 |
| 5,405,996 A * | 4/1995 | Suzuki et al. | 562/548 |
| 5,866,739 A * | 2/1999 | Soled et al. | 585/467 |
| 5,919,725 A * | 7/1999 | Soled et al. | 502/210 |
| 6,534,435 B1 * | 3/2003 | Prasad et al. | 502/208 |
| 6,610,195 B2 * | 8/2003 | Masloboishchikova et al. | 208/137 |
| 6,632,771 B1 | 10/2003 | Maekawa et al. | |

FOREIGN PATENT DOCUMENTS

| | | |
|---|---|---|
| CN | 1351988 A | 11/2000 |
| EP | 0 757 027 A1 | 2/1997 |
| JP | 04-317742 A | 11/1992 |
| JP | 09-067298 A | 3/1997 |
| JP | 09-118647 A | 5/1997 |
| JP | 2000-218160 A | 8/2000 |
| JP | 2001-276623 A | 10/2001 |
| JP | 2002-316048 A | 10/2002 |
| WO | WO 00/74842 A1 | 12/2000 |
| WO | WO 02/00589 A2 | 1/2002 |
| WO | WO 02/20157 A2 | 3/2002 |

* cited by examiner

HETEROPOLYACID AND OR ITS SALT SUPPORTED CATALYST, PRODUCTION PROCESS OF THE CATALYST AND PRODUCTION PROCESS OF COMPOUND USING THE CATALYST

CROSS-REFERENCE TO RELATED APPLICATION

This application is an application filed under 35 U.S.C. § 111(a) claiming benefit pursuant to 35 U.S.C. § 119(e)(1) of the filing date of the Provisional Application 60/436,633 filed Dec. 30, 2002, pursuant to 35 U.S.C. § 111(b).

TECHNICAL FIELD

The present invention relates to a supported catalyst comprising a support having supported thereon a hetero-polyacid and/or a heteropolyacid salt as one of the catalyst components, wherein the heteropolyacid and/or heteropolyacid salt supported is substantially present in a fixed region on the support surface. The present invention also relates to a production process of the catalyst and a process for producing a compound by using the catalyst.

In particular, the supported catalyst of the present invention is useful as a catalyst for the production of a lower aliphatic carboxylic acid by a single-stage contact reaction of a lower olefin and oxygen, or as a catalyst for the production of a lower aliphatic carboxylic acid ester by a reaction of a lower olefin and a lower aliphatic carboxylic acid.

BACKGROUND ART

Heteropolyacids are well known to be useful as acid catalysts or oxidation catalysts. A heteropolyacid and/or heteropolyacid salt supported on a support can prevent the elution of the heteropolyacid or the precipitation of carbonaceous material or increase the surface area to elevate the efficiency in a reaction with a substrate having low affinity for the heteropolyacid. Therefore, the catalyst using a heteropolyacid and/or a heteropolyacid salt as the effective component is generally used as a supported catalyst where the heteropolyacid and/or heteropolyacid salt is supported on a porous support such as silica.

The supported state of the catalyst component in the supported catalyst includes several types. Specific examples thereof include a uniform type, an egg shell type (skin type) and an egg white type. The uniform type, egg shell type and egg white type as used herein each means a supported catalyst in the following state (see, Yoshio ONO et al., *Shokubai no Jiten* (*Dictionary of Catalyst*), 1st ed., 1st imp. pages 102, 108 and 585, Asakura Shoten (Nov. 1, 2000)).

Uniform Type:
So-called uniform distribution or uniform loading.
Egg Shell Type:
This is one of active component distribution states in a support particle or molded body of a supported catalyst and means a state where the active component is present only on the outer surface of the support particle or molded body.
Egg White Type:
This is one of active component distribution states in a support particle or molded body of a supported catalyst and means a state where the active component is present in an inner layer of the support.

The heteropolyacid and/or heteropolyacid salt is used as a supported catalyst, for example, in the hydration of an olefin (see, Japanese Unexamined Patent Publication No. 11-322646 (JP-A-11-322646)) the production of a carboxylic acid ester (see, Japanese Unexamined Patent Publication Nos. 11-263748 and 9-118647 (JP-A-11-263748 and JP-A-9-118647)) and the production of an acetic acid by ethylene oxidation (see, Japanese Unexamined Patent Publication No. 7-89896 (JP-A-7-89896)).

Heretofore, the heteropolyacid and/or heteropolyacid salt has been generally supported in the uniform type. However, the uniform type has a problem that, particularly in a surface-type reaction using the diffusion of raw material as a rate-determining factor, the heteropolyacid and/or heteropolyacid salt supported inside the support may not efficiently participate in the reaction.

On the other hand, as for the method for loading a heteropolyacid in the state other than the uniform type, U.S. Pat. No. 5,919,725 discloses a method of loading a heteropolyacid salt in a specific position slightly inside the surface (so-called egg white type). However, the heteropolyacid salt in the egg white-type catalyst is present inside the support and, in a surface-type reaction of using the diffusion of raw material as a rate-determining factor, cannot make efficient contact with a reactant.

To solve this problem, a catalyst where the heteropolyacid and/or heteropolyacid salt is supported on the surface (so-called egg shell type or skin type) is considered to be more effective.

Particularly, in an oxidation reaction which is a surface-type reaction, it is important to load the catalyst component in the vicinity of surface. For example, JP-A-7-89896 discloses a method of synthesizing an acetic acid from ethylene and oxygen in the presence of a catalyst containing (a) metal palladium and (b) at least one compound selected from heteropolyacids and salts thereof. According to this method, the palladium metal interacts with the heteropolyacid and/or heteropolyacid salt to exert very high activity and selectivity and thereby exhibit excellent activity and selectivity for the production of an acetic acid.

In this example, it is presumed that the metal palladium is supported in the egg shell-type state and the heteropolyacid and/or heteropolyacid salt is, in view of its general loading method on a support, supported in the uniform type. Also in this case, the use efficiency is considered to be elevated by loading the heteropolyacid and/or heteropolyacid salt in the egg shell-type state. Furthermore, when both the metal palladium and the heteropolyacid and/or heteropolyacid salt are supported in the egg shell-type state, these two members can be made present very adjacently and this seems to bring about increase in the probability of interaction and, in turn, production of a higher performance catalyst, In addition, by loading the heteropolyacid and/or heteropolyacid salt in the egg shell-type state, the absolute amount of heteropolyacid and/or heteropolyacid salt can be decreased as compared with the uniform type and this is advantageous in view of profitability and reduction in the cost for recovery and reproduction.

However, a catalyst where a heteropolyacid and/or a heteropolyacid salt is supported in the egg shell-type state, and a production process of the catalyst have been heretofore unknown.

DISCLOSURE OF INVENTION

It is an object of the present invention to provide a heteropolyacid- and/or heteropolyacid salt-supported catalyst having a higher performance, which is used for the production of a compound by various reactions, particularly by a surface reaction.

Another object of the present invention is to provide a production process of the catalyst and a process for producing a compound by using the catalyst.

As a result of extensive investigations for a heteropolyacid- and/or heteropolyacid salt-supported catalyst used in the production of a compound by various reactions, particularly by a surface reaction, which ensures efficient contact of the heteropolyacid and/or heteropolyacid salt with a reaction substrate and thereby exhibits higher performance, the present inventors have found that when the heteropolyacid and/or heteropolyacid salt, as an active component of the catalyst, is supported in the egg shell-type state, a higher performance catalyst can be obtained. The present invention has been accomplished based on this finding.

More specifically, the present invention (I) is a supported catalyst comprising a support having supported thereon one member selected from the group consisting of heteropolyacids and heteropolyacid salts, wherein the at least one heteropolyacid and/or heteropolyacid salt is substantially present in the surface layer region to a depth of 30% from the support surface.

The present invention (II) is a production process of the supported catalyst of the present invention (I).

The present invention (III) is a process for producing a compound by using the supported catalyst of the present invention (I).

Furthermore, the present invention comprises, for example, the following matters.

[1] A supported catalyst comprising a support having supported thereon at least one member selected from the group consisting of heteropolyacids and heteropolyacid salts, wherein the heteropolyacid and/or heteropolyacid salt is substantially present in the surface layer region to a depth of 30% from the support surface.

[2] The catalyst as described in [1] above, wherein 90 mass % or more of the heteropolyacid and/or heteropolyacid salt is present in the surface layer region to a depth of 30% from the support surface.

[3] The catalyst as described in [1] or [2] above, wherein the heteropolyacid is at least one member selected from the group consisting of silicotungstic acid, phosphotungstic acid, phosphomolybdic acid, silicomolybdic acid, silicovanadotungstic acid, phosphovanadotungstic acid, phosphovanadomolybdic acid, silicovanadomolybdic acid, phosphomolybdotungstic acid, silicomolybdotungstic acid, silicovanadotungstic acid, borotungstic acid, boromolybdic acid and tungstomolybdoboric acid.

[4] The catalyst as described in any one of [1] to [3] above, wherein the heteropolyacid salt is either an onium salt of a heteropolyacid or a salt resulting from partially or entirely substituting hydrogen atoms of a heteropolyacid by at least one element selected from metal elements belonging to Groups 1 to 13 in the Periodic Table (*Revised Edition of IUPAC Inorganic Chemistry Nomenclature* (1989)), and the heteropolyacid is selected from the group consisting of silicotungstic acid, phosphotungstic acid, phosphomolybdic acid, silicomolybdic acid, silicovanadotungstic acid, phosphovanadotungstic acid, phosphovanadomolybdic acid, silicovanadomolybdic acid, phosphomolybdotungstic acid, silicomolybdotungstic acid, silicovanadotungstic acid, borotungstic acid, boromolybdic acid and tungstomolybdoboric acid.

[5] The catalyst as described in any one of [1] to [4] above, wherein the support is at least one member selected from the group consisting of silica, diatomaceous earth, montmorillonite, titania, activated carbon, silica alumina, alumina, magnesia, niobia and zirconia.

[6] The catalyst as described in any one of [1] to [5] above, wherein the particle size of the support is from 0.5 to 50 mm.

[7] The catalyst as described in any one of [1] to [6] above, wherein the specific surface area of the support is from 10 to 500 $m^2/g$ and the pore volume is from 0.1 to 3.0 ml/g.

[8] A process for producing the supported catalyst described in any one of [1] to [7] above, comprising the following first to third steps:

First Step:

a step of dissolving a heteropolyacid and/or a heteropolyacid salt in a solvent corresponding to 10 to 40 vol % of the liquid absorption amount of a support to obtain a heteropolyacid and/or heteropolyacid salt solution having a kinematic viscosity of 2.0 to 15.0 cSt (at 40° C.);

Second Step:

a step of impregnating a support with the heteropolyacid and/or heteropolyacid salt solution obtained in the first step to obtain a heteropolyacid and/or heteropolyacid salt-impregnated support; and Third Step:

a step of drying the heteropolyacid and/or heteropolyacid salt-impregnated support obtained in the second step to obtain a heteropolyacid and/or heteropolyacid salt-supported catalyst.

[9] The process as described in [8] above, wherein the solvent is a polar solvent.

[10] The process as described in [9] above, wherein the polar solvent is any one of a lower aliphatic carboxylic acid, a lower aliphatic alcohol or a mixture thereof.

[11] A process for producing a compound, comprising performing a reaction in the presence of the supported catalyst described in any one of [1] to [7] above.

[12] The process as described in [11] above, wherein the reaction is at least one reaction selected from the group consisting of an isomerization reaction, an oxidation reaction, a hydration reaction, a dehydrogenation reaction, an ether-producing reaction, an esterification reaction, a conversion reaction, an acylation reaction, a Ritter reaction and an alkylation reaction.

[13] The process as described in [11] or [12] above, wherein a lower aliphatic olefin and an oxygen are reacted to produce a lower aliphatic carboxylic acid.

[14] The process as described in [13] above, wherein the reaction is performed in the presence of water.

[15] The process as described in [11] or [12] above, wherein a lower olefin and a lower aliphatic carboxylic acid are reacted to produce a lower aliphatic carboxylic acid ester.

[16] The process as described in [15] above, wherein the reaction is performed in the presence of water.

[17] A lower aliphatic carboxylic acid produced by the process described in [13] or [14] above.

[18] A lower aliphatic carboxylic acid ester produced by the process described in [15] or [16] above.

BEST MODE FOR CARRYING OUT THE INVENTION

The preferred embodiments of the present invention are described below.

The "surface layer region to a depth of 30% from the support surface" as used in the present invention (I) varies depending on the shape of support used but follows, for example, the definitions below.

(1) In the Case of Spherical Support

The region means a region covering a distance from the support surface to 30% toward the midpoint in a cross section (FIG. 1) cut to give a maximum area.

(2) In the Case of Cylindrical Support

Figure 2:
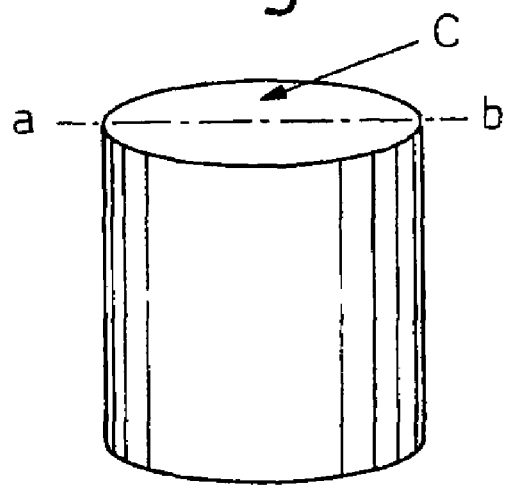
FIG. 2 is a perspective view of a cylindrical support; the line ab is a line of giving a maximum diameter of the circle (C).

The region means a region covering a distance from the support surface to 30% toward the inside of support in a cross section (FIG. 3) obtained by cutting the line ab (FIG. 2).

(3) In the Case of Prismatic Support

Figure 4:
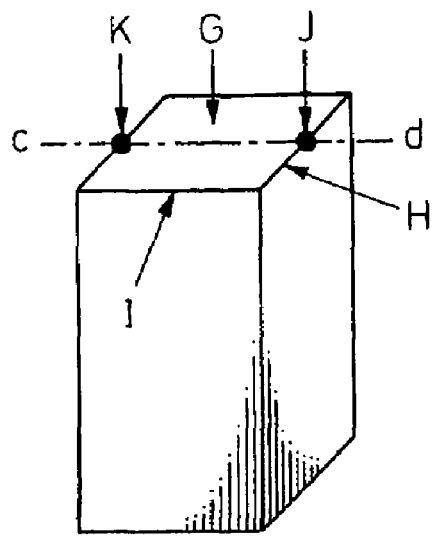
FIG. 4 is a perspective view of a prismatic support; the line cd is a line cutting the support from the midpoint (J) of the side (H) in parallel to the side (I) when the face (G) is a square, and a line cutting the support from the midpoint (J) of the long side (H) in parallel to the short side (I) when the face (G) is a rectangle.

The region means a region covering a distance from the support surface to 30% toward the inside of support in a cross section (FIG. 5) obtained by cutting the line cd (FIG. 4).

(4) In the Case of Cocoon-Like Support

The region means a region covering a distance from the support surface to 30% toward the inside of support in a cross section (FIG. 6) cut to give a maximum area.

(5) In the Case of Pipe-Like Support

Figure 7:
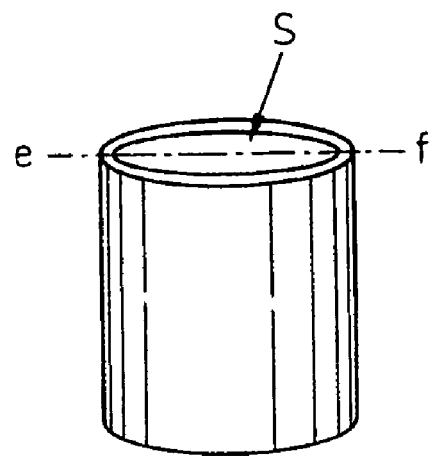
FIG. 7 is a perspective view of a pipe-like support; the line ef is, similarly to the cylindrical support, a line of giving a maximum diameter of the circle (S).

The region means a region covering a distance from the support surface to 30% toward the inside of support in a cross section (FIGS. 8 and 9) obtained by cutting the line ef (FIG. 7).

In the case of a support having a shape not similar to any of these shapes, similarly to those supports, the region indicates a portion in the range covering a distance from the surface to 30%.

In the supported catalyst of the present invention, in view of activity, the heteropolyacid and/or heteropoly-acid salt is preferably present in a larger amount in a portion closer to the support surface. Accordingly, the region where the heteropolyacid and/or heteropolyacid salt exists is preferably closer to the surface and this is preferably a region of 25%, more preferably 20%, from the surface.

The "substantially present in the surface layer region" as used in the supported catalyst of the present invention (I) means such a state that, when the distribution state of heteropolyacid and/or heteropolyacid salt in the supported catalyst is examined, for example, by an analysis method which is described later, the amount of hetero-polyacid and/or heteropolyacid salt is lower than the detection limit in the region except for the specified surface layer region.

Not all heteropolyacid and/or heteropolyacid salt needs to be present in the surface layer region but if the distribution has a gradient to a certain degree, the purpose as the supported catalyst of the present invention (I) can be achieved. The gradient of the distribution is preferably such that 90 mass % or more, preferably 95 mass % or more, more preferably 98 mass % or more of the entire heteropolyacid and/or heteropolyacid salt contained in the catalyst is present in the surface layer region to a depth corresponding to 30% of the radius drawn from the support surface to the center.

In the supported catalyst of the present invention (I), the method for determining the supported distribution of heteropolyacid and/or heteropolyacid salt is not particularly limited and any known method may be used. For example, with respect to the simpler presence of hetero-polyacid and/or heteropolyacid salt, in the case of a colored heteropolyacid and/or heteropolyacid salt, the distribution can be measured by eye. The phosphotungstic acid and silicotungstic acid each is white but is colored by a heat treatment at about 400° C. or more and therefore, such a heteropolyacid may be colored by the heat treatment and the distribution measured by eye.

As for the method of quantitatively measuring the distribution, a measurement, for example, by an electron probe microanalyzer (hereinafter referred to as "EPMA") is preferred. The EPMA as used herein is a device of irradiating a solid substance with an electron probe stopped down to a micron order and performing the elemental analysis or observing the form by utilizing the characteristic X-ray, reflected electron, secondary electron or the like generated from the microfine portion. The EPMA is described in detail in Tsuguro Kinouchi, *EPMA Electron Probe Microanalyzer*, 1st ed., 1st imp., Gijutsu Shoin (Mar. 30, 2002).

The supported distribution of heteropolyacid and/or heteropolyacid salt in the supported catalyst of the present invention is determined by using EPMA according to the following methods. Incidentally, as for the distribution of heteropolyacid and/or heteropolyacid salt, the distribution of tungsten or molybdenum element is measured according to the kind of heteropolyacid supported and this is regarded as the distribution of the corresponding heteropolyacid and/or heteropolyacid salt.

Plane Analysis:

The measurement conditions for the plane analysis are determined by the peak search and the measurement is performed by the plane analysis of three patterns, that is, crystal position of the peak top obtained by the peak search and for the consideration of background, crystal positions shifted before and after the crystal position of the peak top. Based on the measured values, an operation is performed by taking account of the background to obtain plane analysis data. The operation is performed according to the following formula:

$$\text{Plane analysis date} = S - (BG1 + BG2)/2$$

wherein S is an intensity measured at the crystal position of peak top obtained by the peak search and BG1 (background 1) and BG2 (background 2) are intensities at respective measuring points shifted before and after the crystal position of peak top.

Line Analysis:

As the post-treatment of plane analysis data, intensity data for an arbitrary support diameter are taken out to obtain an X-ray intensity profile. The X-ray intensity profile obtained by the line analysis is approximated (corresponds) to the element concentration and therefore, the supported distribution is determined by integrating the X-ray intensity profiles.

The supported distribution of heteropolyacid and/or heteropolyacid salt is determined by using the following method according to the shape of support.

Figure 1:
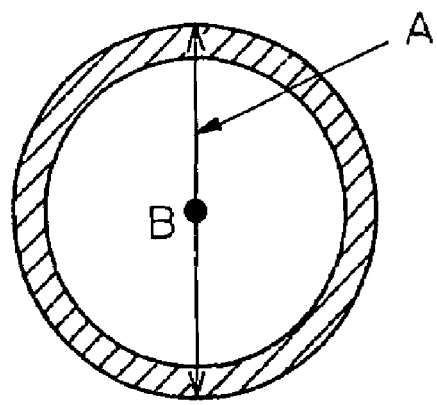
FIG. 1 is a cross-sectional view of a spherical support; A is a long diameter line in the cross section and B is a midpoint of the long diameter line.

In the Case of Spherical Support:

(1) Assuming that the support shape is a true sphere, the support is cut to a cross section of giving a maximum area (FIG. 1).

(2) The cross section is subjected to plane analysis by EPMA and from the plane analysis data, intensity profile data on the long diameter line A are obtained.

(3) From the intensity profile data, the entire integral intensity from the support surface to the midpoint (B) and the entire integral intensity from the support surface to 30% are calculated.

(4) From the ratio of entire integral intensities determined in (3), the supported distribution is calculated.

In the Case of Cylindrical Support:

(1) Assuming that the support shape is a true cylinder, the support is cut at the line ab of giving a maximum diameter of a circle C (FIG. 2).

Figure 3:
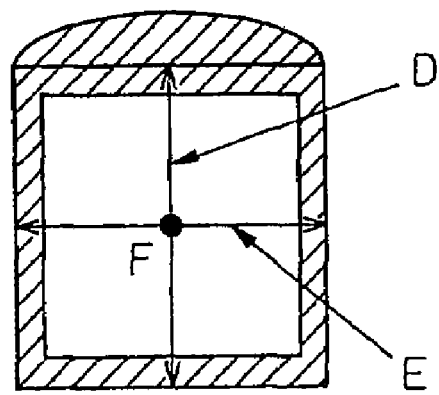
FIG. 3 is a cross-sectional view when the cylindrical support of FIG. 2 is cut at the line ab; D is a long diameter line in this cross section, E is a short diameter line and F is a midpoint of the long diameter line.

(2) The cross section is subjected to plane analysis by EPMA and from the plane analysis data, intensity profile data on the long diameter line D and on the short diameter line E are obtained (FIG. 3). In this case, the short diameter line E is a straight line crossing, at right angles, the midpoint F of the long diameter line D.

(3) From the intensity profile data, the entire integral intensity from the support surface to the midpoint F and the entire integral intensity from the support surface to 30% are calculated on each of the long diameter line D and the short diameter line E.

(4) From the entire integral intensities determined in (3), the supported distribution on each diameter line is calculated.

In the Case of Prismatic Support:

(1) When the face G is a square, the support is cut at the line cd from the midpoint J of the side H in parallel to the side I (FIG. 4). When the face G is a rectangle, the support is cut at the line cd from the midpoint J of the long side H in parallel to the short side I (FIG. 4).

Figure 5:
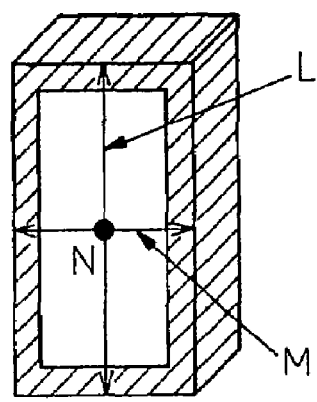
FIG. 5 is a cross-sectional view when the prismatic support of FIG. 4 is cut at the line cd; L is a long diameter line in this cross section, M is a short diameter line and N is a midpoint of the long diameter line.

(2) The cross section is subjected to plane analysis by EPMA and from the plane analysis data, intensity profile data on the long diameter line L and on the short diameter line M are obtained (FIG. 5). In this case, the short diameter line M is a straight line right-angle crossing the midpoint N of the long diameter line L (3) From the intensity profile data, the entire integral intensity from the support surface to the midpoint N and the entire integral intensity from the support surface to 30% are calculated on each of the long diameter line L and the short diameter line M.

(4) From the entire integral intensities determined in (3), the supported distribution on each diameter line is calculated.

Figure 6:
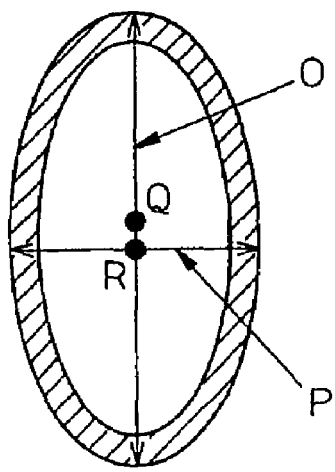
FIG. 6 is a cross-sectional view of a cocoon-like support; O is a long diameter line in this cross section, P is a short diameter line, Q is a midpoint of the long diameter line and R is a midpoint of the short diameter line.

In the Case of Cocoon-Like Support:

(1) The support is cut to a cross section of giving a maximum area (FIG. 6).

(2) The cross section is subjected to plane analysis by EPMA and from the plane analysis data, intensity profile data on the long diameter line O and on the short diameter line P are obtained. The midpoint of the long diameter line O is designated as Q and the midpoint of the short diameter line P is designated as R.

(3) From the intensity profile data, the entire integral intensity from the support surface to the midpoint Q of the long diameter line O and the entire integral intensity from the support surface to 30% are calculated on the long diameter line O. Similarly to the long diameter line O, the entire integral intensity from the support surface to the midpoint R and the entire integral intensity from the support surface to 30% are calculated on the short diameter line P.

(4) From the entire integral intensities determined in (3), the supported distribution on each diameter line is calculated.

In the Case of Pipe-Like Support:

(1) Assuming that the support is a cylindrical support, the support is cut at the line ef of giving a maximum diameter of a circle S similarly to the cylindrical support (FIG. 7).

Figure 8:
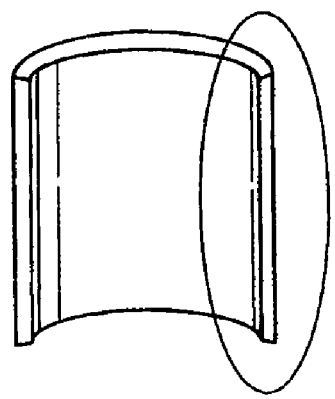
FIG. 8 is a cross-sectional view when the pipe-like support of FIG. 7 is cut at the line ef.
Figure 9:
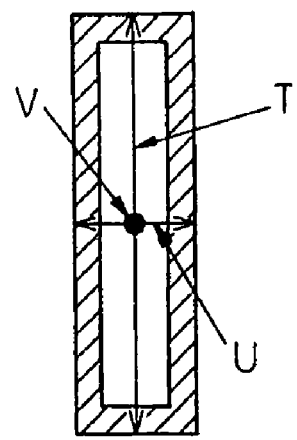
FIG. 9 is an enlarged view of the cross-sectional view of FIG. 8; T is a long diameter line in this cross section, U is a short diameter line and V is a midpoint of the long diameter line.

(2) The cross section is subjected to plane analysis by EPMA and from the plane analysis data, intensity profile data on the long diameter line T and on the short diameter line U are obtained (FIGS. 8 and 9). In this case, the short diameter line U is a straight line crossing, at right angles, the midpoint V of the long diameter line T.

(3) From the intensity profile data, the entire integral intensity from the support surface to the midpoint V and the entire integral intensity from the support surface to 30% are calculated on each of the long diameter line T and the short diameter line U.

(4) From the entire integral intensities determined in (3), the supported distribution on each diameter line is calculated.

As an example of the calculation of supported distribution, the supported distribution of a spherical support is determined according to the following formulae:

$$V_1 = (4/3)\pi(A/2)^3 \quad (1)$$

$$V_2 = (4/3)\pi(0.7(A/2))^3 \quad (2)$$

$$V_3 = V_1 - V_2 \quad (3)$$

$$Wc = (I_2 V_3/(I_1 V_2 + I_2 V_3)) \times 100 \quad (4)$$

wherein (A/2) is a radius (mm) of the support, $\pi$ is a ratio of the circumference of a circle to its diameter, $V_1$ is an entire volume (mm$^3$) of the support, $V_2$ is a volume (mm$^3$) of the support in the region from the support center to 70% of the radius, $V_3$ is a volume (mm$^3$) of the support in the region from the support surface to 30% of the radius, Wc is a percentage (%) of heteropolyacid and/or heteropolyacid salt supported in the region from the support surface to 30% of the radius, $I_1$ is an integral intensity of the X-ray profile from the support center to 70% of the radius obtained by the line analysis, and $I_2$ is an integral intensity of an X-ray profile from the support surface to 30% of the radius obtained by the line analysis.

The heteropolyacid which can be used for the production of the supported catalyst of the present invention comprises a center element and a peripheral element to which oxygen is bonded. The center element is usually silicon or phosphorus but may be one arbitrary element selected from various elements belonging to Groups 1 to 17 of the Periodic Table (*Revised Edition of IUPAC Inorganic Chemistry Nomenclature* (1989)). Specific examples thereof include cupric ion; divalent beryllium, zinc, cobalt and nickel ions; trivalent boron, aluminum, gallium, iron, cerium, arsenic, antimony, phosphorus, bismuth, chromium and rhodium ions; tetravalent silicon, germanium, tin, titanium, zirconium, vanadium, sulfur, tellurium, manganese, nickel, platinum, thorium, hafnium and cerium ions and other rare earth ions; pentavalent phosphorus, arsenic, vanadium and antimony ions; hexavalent tellurium ion; and heptavalent iodide ion, however, the present invention is not limited thereto. Specific examples of the peripheral element include tungsten, molybdenum, vanadium, niobium and tantalum. However, the present invention is not limited thereto.

These heteropolyacids are also known as a "polyoxoanion", "polyoxometallic salt" or "metal oxide cluster". The structures of some well-known anions are named after the researcher in this field and called, for example, Keggin, Wells-Dawson or Anderson-Evans-Perloff structure. These are described in detail in *Poly-San no Kagaku, Kikan Kagaku Sosetsu* (*Chemistry of Polyacid, Quarterly of Chemistry Review*), No. 20, compiled by Nippon Kagaku Kai (1993). The heteropolyacid usually has a high molecular weight, for example, a molecular weight of 700 to 8,500, and includes not only the monomers but also dimeric complexes thereof.

The method for synthesizing the heteropolyacid for use in the supported catalyst of the present invention (I) is not particularly limited and any method may be used. For example, the heteropolyacid can be obtained by heating an acidic aqueous solution containing a salt of molybdic acid or tungstic acid and a simple oxygen acid of hetero atom or a salt thereof (pH: about 1 to 2). For isolating the heteropolyacid compound from the aqueous heteropolyacid solution produced, a method of crystallizing and separating the compound in the form of a metal salt may be used. Specific examples thereof include those described in *Shin Jikken Kagaku Koza* 8, *Muki Kagoubutsu no Gosei (III)* (*New Experimental Chemistry Course* 8, *Synthesis of Inorganic Compounds (III)*), 3rd ed., page 1413, compiled by Nippon Kagaku Kai, issued by Maruzen (Aug. 20, 1984), however, the present invention is not limited thereto. The Keggin structure of the heteropolyacid synthesized can be identified by the chemical analysis or by the X-ray diffraction or UV or IR measurement.

Specific examples of the heteropolyacid include:

| | |
|---|---|
| silicotungstic acid | $H_4[SiW_{12}O_{40}] \cdot xH_2O$ |
| phosphotungstic acid | $H_3[PW_{12}O_{40}] \cdot xH_2O$ |
| phosphomolybdic acid | $H_3[PMo_{12}O_{40}] \cdot xH_2O$ |
| silicomolybdic acid | $H_4[SiMo_{12}O_{40}] \cdot xH_2O$ |
| silicovanadotungstic acid | $H_{4+n}[SiV_nW_{12-n}O_{40}] \cdot xH_2O$ |
| phosphovanadotungstic acid | $H_{3+n}[PV_nW_{12-n}O_{40}] \cdot xH_2O$ |
| phosphovanadomolybdic acid | $H_{3+n}[PV_nMo_{12-n}O_{40}] \cdot xH_2O$ |
| silicovanadomolybdic acid | $H_{4+n}[SiV_nMo_{12-n}O_{40}] \cdot xH_2O$ |
| silicomolybdotungstic acid | $H_4[SiMo_nW_{12-n}O_{40}] \cdot xH_2O$ |
| phosphomolybdotungstic acid | $H_3[PMo_nW_{12-n}O_{40}] \cdot xH_2O$ |

(wherein n is an integer of 1 to 11 and x is an integer of 1 or more). However, the present invention is not limited thereto.

Among these, preferred are silicotungstic acid, phosphotungstic acid, phosphomolybdic acid, silicomolybdic acid, silicovanadotungstic acid and phosphovanadotungstic acid, more preferred are silicotungstic acid, phosphotungstic acid, silicovanadotungstic acid and phosphovanadotungstic acid.

The heteropolyacid salt which can be used in the production of the catalyst of the present invention may be a salt resulting from partially or entirely substituting hydrogen atoms of the above-described heteropolyacid by at least one element selected from metal elements belonging to Groups 1 to 13 in the Periodic Table (*Revised Edition of IUPAC Inorganic Chemistry Nomenclature* (1989)), or an onium salt of the heteropolyacid. Specific examples thereof include metal salts such as lithium, sodium, magnesium, barium, copper, gold, palladium and gallium, and onium salts, however, the present invention is not limited thereto. Among these, lithium salt, sodium salt, gallium salt, copper salt, gold salt and palladium salt are preferred, and lithium salt, sodium salt, copper salt and palladium salt are more preferred.

Examples of the starting material for the element of forming the heteropolyacid salt include lithium nitrate, lithium acetate, lithium sulfate, lithium sulfite, lithium carbonate, lithium phosphate, lithium oxalate, lithium nitrite, lithium chloride, lithium citrate, sodium nitrate, sodium acetate, sodium sulfate, sodium carbonate, monosodium phosphate, disodium phosphate, sodium oxalate, sodium nitrite, sodium chloride, sodium citrate, magnesium nitrate hexahydrate, magnesium acetate tetrahydrate, magnesium sulfate, magnesium carbonate, magnesium phosphate tricosahydrate, magnesium oxalate dihydrate, magnesium chloride, magnesium citrate, barium nitrate, barium acetate, barium sulfate, barium carbonate, barium hydrogenphosphate, barium oxalate monohydrate, barium sulfite, barium chloride, barium citrate, copper nitrate, copper acetate, copper sulfate, copper carbonate, copper diphosphate, copper oxalate, copper chloride, copper citrate, aurous chloride, chloroauric acid, auric oxide, auric hydroxide, auric sulfide, aurous sulfide, palladium nitrate, palladium acetate, palladium sulfate, palladium chloride, gallium dichloride, gallium monochloride, gallium citrate, gallium acetate, gallium nitrate, gallium sulfate, gallium phosphate, ammonium acetate, ammonium carbonate, ammonium nitrate, ammonium dihydrogenphosphate, ammonium hydrogen-carbonate, ammonium citrate, ammonium nitrate, diammonium phosphate, monoammonium phosphate and ammonium sulfate. However, the present invention is by no means limited thereto.

Among these, preferred are lithium nitrate, lithium acetate, lithium carbonate, lithium oxalate, lithium citrate, sodium nitrate, sodium acetate, sodium carbonate, sodium oxalate, sodium citrate, copper nitrate, copper acetate, copper carbonate, copper citrate, aurous chloride, chloroauric acid, palladium nitrate, palladium acetate, gallium citrate, gallium acetate and gallium nitrate, and more preferred are lithium nitrate, lithium acetate, lithium carbonate, lithium oxalate, lithium citrate, sodium nitrate, sodium acetate, sodium carbonate, sodium oxalate, sodium citrate, copper nitrate, copper acetate, copper carbonate, copper citrate, palladium nitrate and palladium acetate.

Specific examples of these heteropolyacid salts include lithium salt of silicotungstic acid, sodium salt of silicotungstic acid, copper salt of silicotungstic acid, gold salt of silicotungstic acid, palladium salt of silicotungstic acid, gallium salt of silicotungstic acid, lithium salt of phosphotungstic acid, sodium salt of phosphotungstic acid, copper salt of phosphotungstic acid, gold salt of phosphotungstic acid, palladium salt of phosphotungstic acid, gallium salt of phosphotungstic acid, lithium salt of phosphomolybdic acid, sodium salt of phosphomolybdic acid, copper salt of phosphomolybdic acid, gold salt of phosphomolybdic acid, palladium salt of phosphomolybdic acid, gallium salt of phosphomolybdic acid, lithium salt of silicomolybdic acid, sodium salt of silicomolybdic acid, copper salt of silicomolybdic acid, gold salt of silicomolybdic acid, palladium salt of silicomolybdic acid, gallium salt of silicomolybdic acid, lithium salt of silicovanadotungstic acid, sodium salt of silicovanadotungstic acid, copper salt of silicovanadotungstic acid, gold salt of silicovanadotungstic acid, palladium salt of silicovanadotungstic acid, gallium salt of silicovanadotungstic acid, lithium salt of phosphovanadotungstic acid, sodium salt of phosphovanadotungstic acid, copper salt of phosphovanadotungstic acid, gold salt of phosphovanadotungstic acid, palladium salt of phosphovanadotungstic acid, gallium salt of phosphovanadotungstic acid, lithium salt of phosphovanadomolybdic acid, sodium salt of phosphovanadomolybdic acid, copper salt of phosphovanadomolybdic acid, gold salt of phosphovanadomolybdic acid, palladium salt of phosphovanadomolybdic acid, gallium salt of phosphovanadomolybdic acid, lithium salt of silicovanadomolybdic acid, sodium salt of silicovanado-molybdic acid, copper salt of silicovanadomolybdic acid, gold salt of silicovanadomolybdic acid, palladium salt of silicovanadomolybdic acid and gallium salt of silicovanado-molybdic acid.

Among these, preferred are lithium salt of silicotungstic acid, sodium salt of silicotungstic acid, copper salt of silicotungstic acid, gold salt of silicotungstic acid, palladium salt of silicotungstic acid, gallium salt of silicotungstic acid, lithium salt of phosphotungstic acid, sodium salt of phosphotungstic acid, copper salt of phosphotungstic acid, gold salt of phosphotungstic acid, palladium salt of phosphotungstic acid, gallium salt of phosphotungstic acid, lithium salt of phosphomolybdic acid, sodium salt of phosphomolybdic acid, copper salt of phosphomolybdic acid, gold salt of phosphomolybdic acid, palladium salt of phosphomolybdic acid, gallium salt of phosphomolybdic acid, lithium salt of silicomolybdic acid, sodium salt of silicomolybdic acid, copper salt of silicomolybdic acid, gold salt of silicomolybdic acid, palladium salt of silicomolybdic acid, gallium salt of silicomolybdic acid, lithium salt of silicovanadotungstic acid, sodium salt of silicovanadotungstic acid, copper salt of silicovanadotungstic acid, gold salt of silicovanadotungstic acid, palladium salt of silicovanadotungstic acid, gallium salt of silicovanadotungstic acid, lithium salt of phosphovanadotungstic acid, sodium salt of phosphovanadotungstic acid, copper salt of phosphovanadotungstic acid, gold salt of phosphovanadotungstic acid, palladium salt of phosphovanadotungstic acid and gallium salt of phosphovanadotungstic acid.

More preferred are lithium salt of silicotungstic acid, sodium salt of silicotungstic acid, copper salt of silicotungstic acid, gold salt of silicotungstic acid, palladium salt of silicotungstic acid, gallium salt of silicotungstic acid, lithium salt of phosphotungstic acid, sodium salt of phosphotungstic acid, copper salt of phosphotungstic acid, gold salt of phosphotungstic acid, palladium salt of phosphotungstic acid, gallium salt of phosphotungstic acid, lithium salt of silicovanadotungstic acid, sodium salt of silicovanadotungstic acid, copper salt of silicovanadotungstic acid, gold salt of silicovanadotungstic acid, palladium salt of silicovanadotungstic acid, gallium salt of silicovanadotungstic acid, lithium salt of phosphovanadotungstic acid, sodium salt of phosphovanadotungstic acid, copper salt of phosphovanadotungstic acid, gold salt of phosphovanadotungstic acid, palladium salt of phosphovanadotungstic acid and gallium salt of phosphovanadotungstic acid.

The amount of the heteropolyacid and/or heteropolyacid salt supported is preferably from 5 to 100 mass %, more preferably from 15 to 70 mass %, based on the entire weight of the support. If the heteropolyacid salt content is less than 5 mass %, the active component content in the catalyst is too small and the activity per unit mass of the catalyst may disadvantageously decrease. If the heteropolyacid salt content exceeds 100 mass %, the effective pore volume decreases and, as a result, the effect owing to the increase in the supported amount may not be brought out and at the same time, coking is liable to occur to seriously shorten the catalyst life or the heteropolyacid on the support surface may be separated.

The support for use in the catalyst of the present invention is not particularly limited and any material may be used insofar as it is a porous substance. Examples thereof include silica, diatomaceous earth, montmorillonite, titania, activated carbon, silica alumina, alumina, magnesia, niobia and zirconia. Among these, preferred are silica, diatomaceous earth, silica alumina and alumina. The particle size is also not particularly limited. The particle size is preferably from 0.5 to 50 mm and in the case of use in a fixed bed, this is preferably from 2 to 10 mm, more preferably from 3 to 7 mm.

The specific surface area of the support is not particularly limited and this is preferably from 10 to 500 $m^2/g$, more preferably from 50 to 350 $m^2/g$, and most preferably from 100 to 300 $m^2/g$.

The pore volume of the support is not particularly limited and this is preferably from 0.1 to 3.0 ml/g, more preferably from 0.5 to 2.0 ml/g.

The present invention (II) is described below. The present invention (II) is a production process of the supported catalyst of the present invention (I).

In the process of the present invention (II), the kinematic viscosity of the heteropolyacid and/or heteropolyacid salt solution at 40° C. is from 2.0 to 15.0 cSt, preferably from 3.0 to 12.0 cSt, more preferably from 4.5 to 10.0 cSt. If the kinematic viscosity is less than 2.0 cSt, the absorption into the support rapidly proceeds and the heteropolyacid and/or heteropolyacid salt cannot be homogeneously supported in the surface layer region of the support, whereas if the kinematic viscosity exceeds 15.0 cSt, the absorption into the support proceeds very slowly and the heteropolyacid and/or heteropolyacid salt solution may not be completely impregnated. As long as the kinematic viscosity at 40° C. is in the range from 2.0 to 15.0 cSt, the temperature of the heteropolyacid and/or heteropolyacid salt solution may be changed.

The method for measuring the kinematic viscosity is not particularly limited and any known method may be used. The kinematic viscosity is preferably measured by a Cannon-Fenske viscometer. The method for measuring the kinematic viscosity by a Cannon-Fenske viscometer is described in *JIS Handbook Kagaku Bunseki* (*JIS Handbook Chemical Analysis*), compiled by Japanese Standards Association, issued by Japanese Standards Association, 1st ed., 1st imp., page 443 (Apr. 20, 1992).

The production process of a supported catalyst of the present invention (II) comprises a first step of dissolving a heteropolyacid and/or a heteropolyacid salt in a solvent corresponding to 10 to 40 vol % of the liquid absorption amount of a support to obtain a heteropolyacid and/or heteropolyacid salt solution having a kinematic viscosity of 2.0 to 15.0 cSt (at 40° C.), a second step of impregnating a support with the heteropolyacid and/or heteropolyacid salt solution obtained in the first step to obtain a heteropolyacid and/or heteropolyacid salt-impregnated support, and a third step of drying the heteropolyacid and/or heteropolyacid salt-impregnated support obtained in the second step to obtain a heteropolyacid and/or heteropolyacid salt-supported catalyst.

In the first step, a heteropolyacid and/or a heteropolyacid salt is dissolved in a solvent to obtain a heteropolyacid and/or heteropolyacid salt solution having a kinematic viscosity of 2.0 to 15.0 cSt (at 40° C.). The solvent is used in an amount corresponding to 10 to 40 vol % of the liquid absorption amount of a support. If the amount of the solvent is less than 10 vol % of the liquid absorption amount of a support, the heteropolyacid and/or heteropolyacid salt may not be completely dissolved, whereas if it exceeds 40 vol %, the heteropolyacid and/or heteropolyacid salt may be absorbed even into the inside of the support.

In the second step, a support is impregnated with the heteropolyacid and/or heteropolyacid salt solution obtained in the first step to obtain a heteropolyacid and/or heteropolyacid salt-impregnated support. In this case, the support may be a catalyst precursor having supported thereon other metal component or the like. More specifically, on a support having supported on the surface thereof a metal such as palladium, the heteropolyacid and/or heteropolyacid salt may be supported to lie on the metal.

In the third step, the heteropolyacid and/or heteropolyacid salt-impregnated support obtained in the second step is dried to obtain a heteropolyacid and/or heteropolyacid salt-supported catalyst. The timing of starting the drying subsequently to the impregnation treatment greatly varies depending on the size of support and the kinematic viscosity of heteropolyacid and/or heteropolyacid salt. However, if the support after the impregnation is left standing as it is, the heteropolyacid and/or heteropolyacid salt may be absorbed into the inside of the support, therefore, the support is preferably dried immediately after the impregnation.

The drying is performed, for example, in a hot air stream by using an air-blasting drier or in an inert gas stream in a drying room. For example, the drying can be performed in a stream of nitrogen or carbon dioxide. Depending on the case, the drying is performed under reduced pressure, preferably at 0.01 to 0.08 MPa.

The residual solvent content after the drying is preferably 10 mass % or less. If the solvent remains in the catalyst, the heteropolyacid and/or heteropolyacid salt may be absorbed even into the inside of the support. After the drying, the catalyst is suitably cooled to an ambient temperature in a desiccator so as not to absorb moisture.

If desired, the supported catalyst after the drying in the third step may be treated with a gas containing a reducing gas. In the case of reducing the catalyst, the reduction may be performed by using a gaseous reducing agent. The reducing temperature is usually from 40 to 350° C., preferably from 70 to 200° C. In general, the reduction is preferably performed by using a reducing agent diluted with an inert gas containing from 0.01 to 80 vol %, preferably from 0.5 to 50 vol %, of a reducing agent. Examples of the inert gas which is used include nitrogen, carbon dioxide and a rare gas. Suitable examples of the reducing agent include hydrogen, methanol, formaldehyde, ethylene, propylene, isobutylene, butylene and other olefins.

However, if the temperature at the drying or reducing treatment after the heteropolyacid and/or heteropolyacid salt is supported exceeds about 350° C., the skeleton of the heteropolyacid may be broken.

In the supported catalyst obtained as above, the amount of the heteropolyacid and/or heteropolyacid salt supported can be simply calculated by subtracting the weight of support from the weight of catalyst obtained after drying. The amount supported can be more exactly determined by a chemical analysis such as induction coupled plasma emission spectroscopic analysis (ICP), fluorescent X-ray analysis and atomic absorption analysis.

The solvent which can be used in the first step is not particularly limited and any solvent may be used as long as it can homogeneously dissolve or suspend the desired heteropolyacid and/or heteropolyacid salt. An organic solvent or the like which can be easily removed by drying after the impregnation treatment is used. The solvent is preferably a polar solvent. Examples of the polar solvent include a lower aliphatic carboxylic acid and a lower aliphatic alcohol. Specific examples thereof include acetic acid, methanol and ethanol. In this solvent, water may be contained. Also, a water content derived from the hydrate of heteropolyacid may be contained.

The present invention (III) is described below. The present invention (III) is a process for producing a compound by using the supported catalyst of the present invention (I).

The supported catalyst of the present invention (I) can be used for a reaction system containing a heteropoly-acid and/or a heteropolyacid salt as the catalyst component. Examples of the reaction system include a surface reaction and a diffusion-controlled reaction. Specific examples thereof include an isomerization reaction (see, Japanese Unexamined Patent Publication No. 2002-105001 (JP-A-2002-105001)), an oxidation reaction (see, JP-A-7-89896 and Japanese Unexamined Patent Publication No. 2000-308830 (JP-A-2000-308830)), a hydration reaction (see, JP-A-11-322646), a dehydrogenation reaction (see, Japanese Unexamined Patent Publication No. 2001-232207 (JP-A-2001-232207)), an ether producing reaction (see, Japanese Unexamined Patent Publication No. 7-76540 (JP-A-7-76540)), an esterification reaction (see, JP-A-11-263748 and JP-A-9-118647), a conversion reaction (see, Japanese Unexamined Patent Publication No. 2001-29789 (JP-A-2001-29789)), an acylation reaction (see, Japanese Unexamined Patent Publication No. 10-237020 (JP-A-10-237020)), a Ritter reaction (see, Japanese Unexamined Patent Publication No. 10-175933 (JP-A-10-175933)) and/or an alkylation reaction (see, Japanese International Application Domestic Publication No. 10-508300 (JP-A-10-508300)). Among these, preferred are an oxidation reaction and an esterification reaction.

Examples of the oxidation reaction include a reaction of synthesizing an acetic acid from ethylene and oxygen in the presence of a catalyst containing at least one compound selected from (a) metal palladium and (b) a heteropolyacid or a salt thereof (see, JP-A-7-89896).

Examples of the esterification reaction include a reaction of synthesizing a corresponding ester from a lower aliphatic carboxylic acid and an olefin in the presence of a heteropolyacid and/or heteropolyacid salt catalyst supported on a siliceous support (see, Japanese Unexamined Patent Publication No. 11-269126 (JP-A-11-269126) and JP-A-11-263748).

The present invention is further illustrated below by referring to examples and comparative examples, however, these examples are set forth only to show the outline of the present invention, and the present invention is not limited by these examples.

Reagent:

The following reagents were used.

Palladium Acetate:

Produced by Wako Pure Chemical Industries, Ltd.

Aqueous Sodium Tetrachloropalladate Solution:

Produced by N.E. Chemcat Corporation (Pd=20.48 mass %)

Aqueous Chloroauric Acid Solution:

Chloroauric acid produced by N.E. Chemcat Corporation (Au=23.89 mass %) was diluted with distilled water to obtain an aqueous solution of Au=10 mass %.

Aqueous Zinc Chloride Solution:

Zinc chloride produced by Wako Pure Chemical Industries, Ltd. was dissolved in distilled water to obtain an aqueous solution of Zn=5 mass %.

Sodium Metasilicate Nonahydrate:

Produced by Wako Pure Chemical Industries, Ltd.

Aqueous Hydrazine Monohydrate Solution:

Hydrazine monohydrate produced by Wako Pure Chemical Industries Ltd. was diluted with distilled water to obtain an aqueous solution of hydrazine=0.53 g/ml.

Sodium Tellurite:

Produced by Wako Pure Chemical Industries, Ltd.

Telluric Acid:

Produced by Kanto Kagaku

Silicotungstic Acid Hexacosahydrate:

Produced by Nippon Inorganic Colour & Chemical Co., Ltd.

Support:

Synthetic silica was used as the support.

EXAMPLE 1

Production and Evaluation of Catalyst A

An aqueous sodium tetrachloropalladate solution (4.883 g), 4.0 g of an aqueous chloroauric acid solution and 1.08 g of a zinc chloride solution were diluted with 38 ml (corresponding to 100 vol % of the liquid absorption amount of support) of distilled water and thereto, 40.4 g of a support (spherical, diameter: about 5 mmϕ) was added and completely impregnated with the solution. The resulting support was added to 80 ml of an aqueous solution containing 8.119 g of sodium metasilicate nonahydrate and left standing for 20 hours. Thereto, 11 ml of an aqueous hydrazine monohydrate solution was added and, after washing with water, the support was dried at 110° C. for 4 hours (Supported Body A). Thereafter, Supported Body A was added to 38 ml (corresponding to 100 vol % of the liquid absorption amount of support) of an aqueous solution containing 0.208 g of sodium tellurite, impregnated with the solution, air-dried for 1 hour, washed with water and then dried at 110° C. for 4 hours (Supported Body B). Subsequently, Supported Body B was charged in a solution prepared by dissolving 20.704 g of silicotungstic acid hexacosahydrate in 13 ml (corresponding to 35 vol % of the liquid absorption amount of support) of acetic acid and immediately after the entire solution was absorbed, dried at 110° C. for 4 hours to obtain 61.82 g of Catalyst A.

Catalyst A prepared as above was analyzed by EPMA and it was found that 95% or more of tungsten was present in the region to a depth of 30% of the radius.

In a stainless steel-made reaction tube having an internal diameter of 21.4 mm, 5 ml of Catalyst A obtained and 11 ml of a diluting support were filled and a reaction was performed at a temperature of 200° C. and a pressure of 0.8 MPaG (gauge pressure) by introducing a mixed gas consisting of 10% of ethylene, 6% of oxygen, 25% of water and 59% of nitrogen at a flow rate of 45 Nl/H. The gas produced was cooled and condensed and the collected reaction solution was analyzed by gas chromatography. As a result, the space time yield of acetic acid was 525 g/1H, the acetic acid selectivity was 87.9% and the carbon dioxide selectivity was 5.9%.

COMPARATIVE EXAMPLE 1

Production and Evaluation of Catalyst B

Catalyst B (61.81 g) was obtained by repeating the same operation as in Example 1 except that 38 ml (corresponding to 100 vol % of the liquid absorption amount of support) of an aqueous solution having dissolved therein 20.704 g of silicotungstic acid hexacosahydrate was used at the time of loading silicotungstic acid.

Catalyst B prepared as above was analyzed by EPMA and found that the tungsten was homogeneously supported in the entire support.

A reaction was performed under the same conditions as in Example 1, as a result, the space time yield of acetic acid was 489 g/1H, the acetic acid selectivity was 87.9% and the carbon dioxide selectivity was 7.7%.

EXAMPLE 2

Production of Catalyst C

In a solution prepared by dissolving 0.78 g of palladium acetate and 10.352 g of silicotungstic acid hexacosahydrate in 6.5 ml (corresponding to 35 vol % of the liquid absorption amount of support) of acetic acid, 20.2 g of a support (spherical, diameter: about 5 mmϕ) was added and after impregnating the solution, dried at 110° C. for 4 hours in a drier (Supported Body C). Then, Supported Body C obtained was filled in a glass-made reaction tube having an internal diameter of 40 mm and reduced at a temperature of 200° C. under atmospheric pressure for 3 hours by introducing a mixed gas consisting of 50% of nitrogen and 50% of hydrogen at a flow rate of 18 Nl/hr to obtain 29.75 g of Catalyst C. Catalyst C prepared as above was analyzed by EPMA and it was found that 95% or more of tungsten was present in the region to a depth of 30% of the radius.

Analysis Method of Condensate:

Using an analytical solution prepared by adding 10 ml of distilled water to a condensate, the analysis was performed by an internal standard method.

As the internal standard, 100 µl of 1,4-dioxane was added per 10 ml of the analytical solution. The analysis was performed by injecting its 0.3 µl portion under the following conditions.

1. Acetic Acid

Gas Chromatography:
   GC-9A, manufactured by Shimadzu Corporation

Column:
   packed column, 5% Thermon-3000 Shincarbon A, 60 to 80 mesh (length: 3 m)

Carrier Gas:
   nitrogen (column flow rate: 2.5 ml/min)

Temperature Conditions:
   The detector and vaporization chamber were at a temperature of 180° C. and the column temperature was elevated up to 150° C. at a temperature rising rate of 10° C./min from the initiation of analysis.

Detector:
   FID ($H_2$ pressure: 60 KPa, air pressure: 100 KPa)

2. Trace By-Products

Gas Chromatography:
   GC-14B, manufactured by Shimadzu Corporation

Column:
   capillary column (length: 30 m, internal diameter: 0.25 mm, film thickness: 0.5 µm)

Carrier Gas:
   nitrogen (split ratio: 20, column flow rate: 1 ml/min)

Temperature Conditions:
   The detector and vaporization chamber were at a temperature of 200° C. and the column temperature was kept at 37° C. for 7 minutes from the initiation of analysis, then elevated to 50° C. at a temperature rising rate of 10° C./min, kept at 50° C. for 4 minutes, thereafter elevated to 150° C. at a temperature rising rate of 20° C./min, kept at 150° C. for 7 minutes, further elevated to 230° C. at a temperature rising rate of 20° C./min and kept at 230° C. for 15 minutes.

Detector:
   FID ($H_2$ pressure: 60 KPa, air pressure: 100 KPa)

Analysis Method of Uncondensed Gas:
   Using an absolute calibration curve method, the analysis was performed under the following conditions by sampling 50 ml of the uncondensed gas and passing the entire amount thereof into a 1 ml-volume gas sampler attached to the gas chromatograph.

1. Oxygen, Nitrogen and Carbon Monoxide

Gas Chromatograph:
   gas chromatography (GC-12A, manufactured by Shimadzu Corporation) with a gas sampler (MGS-4, measuring tube: 1 ml) for Shimadzu gas chromatograph Column:
   packed column MS-5A IS, 60 to 80 mesh (length: 3 m)

Carrier Gas:
   helium (flow rate: 2.5 ml/min)

Temperature Conditions:
   The detector and vaporization chamber were at a temperature of 110° C., and the column temperature was 70° C. and constant.

Detector:
   TCD (He pressure: 70 KPa, current: 100 MA, temperature: 110° C.)

2. Ethan, Carbon Dioxide and Ethylene

Gas Chromatograph:
   gas chromatography (GC-9A, manufactured by Shimadzu Corporation) with a gas sampler (MGS-4, measuring tube: 1 ml) for Shimadzu gas chromatograph Column:
   packed column Unibeads IS, 60 to 80 mesh (length: 3 m)

Carrier Gas:
   helium (flow rate: 40 ml/min)

Temperature Conditions:
   The detector and vaporization chamber were at a temperature of 100° C. and the column temperature was 60° C. and constant.

Detector:
   TCD (He pressure: 70 KPa, current: 100 mA, temperature: 100° C.)

Measuring Method of Supported Distribution:

Pretreatment

Resin Embedding:
   Cold Embedding Resin No. 105 produced by Marumoto Struers K.K. was used by mixing thereto a hardening agent for No. 105.

Cutting:
   Cut by Isomet (wet diamond cutter). For the refrigerant, a solvent in which a heteropolyacid and/or a heteropolyacid salt does not dissolve, such as hexane, was selected.

Vapor Deposition:
   Platinum was used as the vapor deposition substance.

Apparatus:
   JXA-8900 manufactured by JEOL Ltd.

EPMA Analysis

X-Ray Detector:
   Wavelength dispersion spectroscopy (WDS).
Acceleration voltage: 15 kV
Irradiation current: $1 \times 10^{-7}$ A Peak Search Conditions (Tungsten)
Spectral crystal: PETH
Spectral crystal range: 210 to 240 mm
Spectral crystal step: 30 μm
Integration time: 200 msec Measurement Conditions in Plane Analysis (Tungsten)
Spectral crystal: PETH
Spectral crystal position:
   223.556 mm (signal), 219.6 mm (background 1), 225.6 mm (background 2)
Measurement point distance:
   X: 20 μm, Y: 20 μm (the measurement region was appropriately set to enclose the catalyst)
Measurement time: 30 msec×1
Scan: stage scan Data Processing:
   (1) A data operation was performed by taking account of background to obtain plane analysis data (background correction).
   (2) Lines (9 lines) were drawn by rotating the angle in steps of 20° with respect to the plane analysis data operated in (1) and intensity profile data were obtained every each line (line analysis).
   (3) The entire integral intensity from the support surface to the support center was calculated.
   (4) The entire integral intensity from the support surface to 30% was calculated.
   (5) From the integral intensity ratio determined in (3) and (4), the supported distribution was calculated.

INDUSTRIAL APPLICABILITY

As described in the foregoing pages, according to the present invention, a so-called egg shell-type supported catalyst where a heteropolyacid and/or a heteropolyacid salt is present in the surface layer region of the support can be obtained and this enables an elevation of use efficiency of the heteropolyacid and/or heteropolyacid salt and, as a result, a supported catalyst having high activity can be provided.

The invention claimed is:

1. A supported catalyst comprising a support having a support surface, and supported on the support at least one member selected from the group consisting of heteropolyacids and heteropolyacid salts, wherein 90 mass % or more of the heteropolyacid and/or heteropolyacid salt is present in a surface layer region that extends from the support surface to a distance from the support surface of 30% toward the midpoint in a cross section of the support.

2. The catalyst according to claim 1, wherein the support is spherical.

3. A catalyst according to claim 1, wherein the heteropolyacid is at least one member selected from the group consisting of silicotungstic acid, phosphotungstic acid, phosphomolybdic acid, silicomolybdic acid, silicovanadotungstic acid, phosphovanadotungstic acid, phosphovanadomolybdic acid, silicovanadomolybdic acid, phosphomolybdotungstic acid, silicomolybdotungstic acid, silicovanadotungstic acid, borotungstic acid, boromolybdic acid and tungstomolybdoboric acid.

4. A catalyst according to claim 1, wherein the heteropolyacid salt is either an onium salt of a heteropolyacid or a salt resulting from partially or entirely substituting hydrogen atoms of a heteropolyacid by at least one element selected from metal elements belonging to Groups 1 to 13 in the Periodic Table, and the heteropolyacid is selected from the group consisting of silicotungstic acid, phosphotungstic acid, phosphomolybdic acid, silicomolybdic acid, silicovanadotungstic acid, phosphovanadotungstic acid, phosphovanadomolybdic acid, silicovanadomolybdic acid, phosphomolybdotungstic acid, silicomolybdotungstic acid, silicovanadotungstic acid, borotungstic acid, boromolybdic acid and tungstomolybdoboric acid.

5. A catalyst according to claim 1, wherein the support is at least one member selected from the group consisting of silica, diatomaceous earth, montmorillonite, titania, activated carbon, silica alumina, alumina, magnesia, niobia and zirconia.

6. A catalyst according to claim 1, wherein the support has a particle size of from 0.5 to 50 mm.

7. A catalyst according to claim 1, wherein the support has a specific surface area of from 10 to 500 $m^2/g$ and a pore volume from 0.1 to 3.0 ml/g.

8. A process for producing a supported catalyst as described in claim 1, comprising the following first to third steps:

First Step:
a step of dissolving a heteropolyacid and/or a heteropolyacid salt in a solvent corresponding to 10 to 40 vol % of the liquid absorption amount of a support to obtain a heteropolyacid and/or heteropolyacid salt solution having a kinematic viscosity of 2.0 to 15.0 cSt (at 40° C.);

Second Step:
a step of impregnating a support with the heteropolyacid and/or heteropolyacid salt solution obtained in the first step to obtain a heteropolyacid and/or heteropolyacid salt-impregnated support; and Third Step:
a step of drying the heteropolyacid and/or heteropolyacid salt-impregnated support obtained in the second step to obtain a heteropolyacid and/or heteropolyacid salt-supported catalyst.

9. A process according to claim 8, wherein the solvent is a polar solvent.

10. A process according to claim 9, wherein the polar solvent is any one of a lower aliphatic carboxylic acid, a lower aliphatic alcohol or a mixture thereof.

11. A process, for producing a compound, comprising performing a reaction in the presence of a supported catalyst as described in claim 1.

12. A process according to claim 11, wherein the reaction is at least one reaction selected from the group consisting of an isomerization reaction, an oxidation reaction, a hydration reaction, a dehydrogenation reaction, an ether-producing reaction, an esterification reaction, a conversion reaction, an acylation reaction, a Rifler reaction and an alkylation reaction.

13. A process according to claim 11 or 12, wherein a lower aliphatic olefin and an oxygen are reacted to produce a lower aliphatic carboxylic acid.

14. A process according to claim 13, wherein the reaction is performed in the presence of water.

15. A process according to claim 11 or 12, wherein a lower olefin and a lower aliphatic carboxylic acid are reacted to produce a lower aliphatic carboxylic acid ester.

16. A process according to claim 15, wherein the reaction is performed in the presence of water.

* * * * *